(12) United States Patent
Collingwood et al.

(10) Patent No.: US 7,947,730 B2
(45) Date of Patent: May 24, 2011

(54) PIPERIDINIUM AND PYRROLIDINIUM DERIVATIVES AS LIGANDS FOR THE MUSCARINIC M3 RECEPTOR

(75) Inventors: Stephen Paul Collingwood, West Sussex (GB); Urs Baettig, West Sussex (GB); Clive McCarthy, Basel (CH)

(73) Assignee: Novartis AG, Basel (CH)

( * ) Notice: Subject to any disclaimer, the term of this patent is extended or adjusted under 35 U.S.C. 154(b) by 1355 days.

(21) Appl. No.: 10/561,366

(22) PCT Filed: Jun. 23, 2004

(86) PCT No.: PCT/EP2004/006795
§ 371 (c)(1),
(2), (4) Date: May 15, 2006

(87) PCT Pub. No.: WO2005/000815
PCT Pub. Date: Jan. 6, 2005

(65) Prior Publication Data
US 2006/0287362 A1    Dec. 21, 2006

(30) Foreign Application Priority Data

Jun. 24, 2003 (GB) .................................. 0314697.4
Nov. 26, 2003 (GB) .................................. 0327526.0

(51) Int. Cl.
*A61K 31/40* (2006.01)
*C07D 409/14* (2006.01)
(52) U.S. Cl. ........ 514/422; 514/317; 514/326; 514/408; 546/212; 546/231; 548/471; 548/527
(58) Field of Classification Search .................. 514/317, 514/326, 408, 422; 546/212, 231; 548/471, 548/527
See application file for complete search history.

(56) References Cited

U.S. PATENT DOCUMENTS

| 2,746,966 | A |   | 5/1956 | Biel et al. |            |
|-----------|---|---|--------|-------------|------------|
| 3,240,784 | A |   | 3/1966 | Flick et al. |           |
| 4,447,439 | A | * | 5/1984 | Nishimura et al. | ...... 514/217.04 |
| 6,307,060 | B1|   | 10/2001 | Noe et al. |           |
| 7,399,861 | B2| * | 7/2008 | Bodor | .............................. 546/91 |

FOREIGN PATENT DOCUMENTS

| EP | 0 073 645   | 3/1983 |
| EP | 1 302 458   | 4/2003 |
| EP | 0823423     | 6/2004 |
| WO | 92/06958    | 4/1992 |
| WO | WO 98/21183 | 5/1998 |
| WO | 03/087094   | 10/2003 |

OTHER PUBLICATIONS

Prat et al. "Preparation of acyloxypyrrolidinium . . ." CA 139:337885 (2003).*

Kutsuma, et al., "1-(1,3-Dioxoan-4-ylmethyl)piperdinol Derivatives", Chemical Abstracts, Database Accession No. 1978:6859 and JP 52 083763, Jul. 12, 1977.
Kutsuma et al., "Stereoisomers of 4-acyloxy-1-alkyl-1-(1,3-dioxoran-4-ylmethyl)piperidinium Salt Derivatives", Chemical Abstracts, Database Accession No. 1979:405219 and JP 54 027570, Mar. 1, 1979.
"4-Acyloxy-1-(1,3-dioxolan-2-ylmethyl)piperidine Derivatives", Chemical Abstracts, Database Accession No. 1981:603921 and JP 56 079688, Jun. 30, 1981.
".Alpha.-Cyclic Aminophenylacetic Acid Esters and Their Quarternary Ammonium Salts", Chemical Astracts, Database Accession No. 1984:120902 and JP 58 208270, Dec. 3, 1983.
Yoshida et al., "Structure-Activity Relationship of 3- and 4-acyloxy-1-(1,3-dioxolan-4-ylmethyl)piperidine Derivatives", Chemical and Pharmaceutical Bulletin, vol. 33, No. 2, pp. 818-822 (1985).
Sugai et al., "Studies on Spasmolytics. II. Synthesis and Anticholinergic Activities of 4-acyloxy-1-alkyl-1-(1,3-dioxolan-4-ylmethyl)piperidinium Compounds", Chemical and Pharmaceutical Bulletin, vol. 32, No. 3, pp. 977-985 (1984).
Sugai et al., "Studies on Spasmolytics. III. Synthesis and Anticholinergic Activityof 4-(acyloxy)-1-(1,3-dioxolan-2-ylmethyl)piperidines and Their Quarternary Salts", Chemical and Pharmaceutical Bulletin, vol. 32, No. 3, pp. 1126-1134 (1984).
Kajiwara et al., "Studies on Spasmolytics. VI. Pharmacological Studies of Stereoisomeric 1,4-trans- and . . . ", Chemical Abstracts, Database Accession No. 1986:14939 and Yakugaku Zasshi, vol. 105, No. 10, pp. 983-989 (1985).
Waelbroeck et al., "Binding Properties of Nine 4-diphenyl-acetoxy-N-methylpiperidine (4-DAMP) Analogs to M1, M2, M3 and Putative M4 Muscarinic Receptor Subtypes", British Journal of Pharmacology, vol. 105, No. 1, pp. 97-102 (1992).
Freeman, "Antispasmodics IV. Further basic alkyl ester acid addition & quaternary ammonium salts", J. Am. Pharm. Assoc., vol. XLV, No. 8, pp. 578-581, (1956).
Abstract of Ji et al., "Studies on a soft glycopyrrolate analog SG-1", Pharmazie, vol. 57, No. 2, pp. 138-141, (2002).
Barlow et al., "A further search for selective antagonists at M2 muscarinic receptors", Br. J. Pharmacol., vol. 89, No. 4, pp. 837-843, (1986).

* cited by examiner

*Primary Examiner* — Celia Chang
(74) *Attorney, Agent, or Firm* — Cozette M McAvoy

(57) ABSTRACT

Compounds of formula I

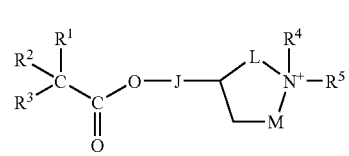

in salt or zwitterionic form wherein, wherein $R^1$, $R^2$, $R^3$, $R^4$, $R^5$, J, L and M have the meanings as indicated in the specification, are useful for treating conditions that are mediated by the muscarinic M3 receptor. Pharmaceutical compositions that contain the compounds and a process for preparing the compounds are also described.

9 Claims, No Drawings

PIPERIDINIUM AND PYRROLIDINIUM DERIVATIVES AS LIGANDS FOR THE MUSCARINIC M3 RECEPTOR

This invention relates to organic compounds, their preparation and use as pharmaceuticals.

In one aspect the invention provides compounds of formula I

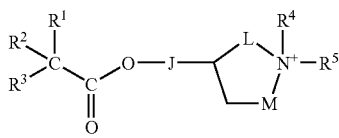

in salt or zwitterionic form wherein
$R^1$ and $R^3$ are each independently a $C_3$-$C_{15}$-carbocyclic group or a 5- to 12-membered heterocyclic group having at least one ring heteroatom selected from nitrogen, oxygen and sulphur;
$R^2$ is hydrogen, hydroxy, or $C_1$-$C_4$-alkyl optionally substituted by hydroxy;
L and M are (a bond and —$CH_2$—$CH_2$—), (—$CH_2$— and —$CH_2$—$CH_2$—) or (—$CH_2$—$CH_2$— and —$CH_2$—) respectively and J is $C_1$-$C_2$-alkylene,
or L and M are (—$CH_2$— and —$CH_2$—$CH_2$—) or (—$CH_2$—$CH_2$— and —$CH_2$—) respectively and J is a bond;
$R^4$ is $C_1$-$C_4$-alkyl;
$R^5$ is $C_1$-alkyl substituted by —SO—$R^6$, —S(=O)$_2$—$R^6$, —CO—$R^6$, —CO—O—$R^6$, —CO—NH—$R^6$ or —$R^7$,
or $R^5$ is $C_2$-$C_{10}$-alkyl substituted by —O—$R^6$, —S—$R^6$, —SO—$R^6$, —S(=O)$_2$—$R^6$, —CO—$R^6$, —O—CO—$R^6$, —O—CO—$R^6$, —CO—O—$R^6$, —NH—CO—$R^6$, —CO—NH—$R^6$, —$R^7$ or —$R^8$,
or $R^5$ is $C_2$-$C_{10}$-alkenyl or $C_2$-$C_{10}$-alkynyl optionally substituted by —$R^7$ or —$R^8$;
$R^6$ is a $C_3$-$C_{15}$-carbocyclic group or a 5- to 12-membered heterocyclic group having at least one ring heteroatom selected from nitrogen, oxygen and sulphur,
or $R^6$ is $C_1$-$C_{10}$-alkyl optionally substituted by $C_1$-$C_{10}$-alkoxy, —O—$R^7$, a $C_3$-$C_{15}$-carbocyclic group or a 5- to 12-membered heterocyclic group having at least one ring heteroatom selected from nitrogen, oxygen and sulphur;
$R^7$ is a 5- to 12-membered heterocyclic group having at least one ring heteroatom selected from nitrogen, oxygen and sulphur; and
$R^8$ is a $C_3$-$C_{15}$-carbocyclic group.

Terms used in the specification have the following meanings:

"Optionally substituted" means the group referred to can be substituted at one or more positions by any one or any combination of the radicals described.

"Halo" or "halogen" as used herein denotes an element belonging to group 17 (formerly group VII) of the Periodic Table of Elements, which may be, for example, fluorine, chlorine, bromine or iodine. Preferably halo or halogen is fluorine, chlorine or bromine.

"$C_1$-$C_{10}$-alkyl" as used herein denotes straight chain or branched alkyl having 1 to 10 carbon atoms. Preferably, $C_1$-$C_{10}$-alkyl is $C_1$-$C_5$-alkyl, e.g. $C_1$-$C_4$-alkyl.

"$C_1$-$C_{10}$-alkylene" as used herein denotes straight chain or branched alkylene having 1 to 10 carbon atoms. Preferably, $C_1$-$C_{10}$-alkylene is $C_1$-$C_4$-alkylene.

"$C_2$-$C_{10}$-alkenyl" as used herein denotes straight chain or branched alkenyl having 2 to 10 carbon atoms. Preferably, $C_2$-$C_{10}$-alkenyl is $C_2$-$C_4$-alkenyl.

"$C_2$-$C_{10}$-alkynyl" as used herein denotes straight chain or branched alkynyl having 2 to 10 carbon atoms. Preferably, $C_2$-$C_{10}$-alkynyl is $C_2$-$C_8$-alkynyl, e.g. $C_2$-$C_4$-alkynyl.

"$C_1$-$C_{10}$-alkoxy" as used herein denotes straight chain or branched alkoxy having 1 to 10 carbon atoms. Preferably, $C_1$-$C_{10}$-alkoxy is $C_1$-$C_4$-alkoxy.

"$C_3$-$C_{15}$-carbocyclic group" as used herein denotes a carbocyclic group having 3 to 15 ring carbon atoms, for example a monocyclic group, either cycloaliphatic, such as a $C_3$-$C_8$-cycloalkyl, for example cyclopentyl, cyclohexyl, cycloheptyl or cyclooctyl, or aromatic, such as phenyl, which can be substituted by one or more, usually one or two, $C_1$-$C_4$-alkyl groups, or a bicyclic group, such as a $C_8$-bicyclic, $C_9$-bicyclic or $C_{10}$-bicyclic group, which could be cycloaliphatic or could be aromatic, such as indanyl, indenyl or naphthyl, again any of which can be substituted by one or more, usually one or two, $C_1$-$C_4$-alkyl groups. Preferably the $C_3$-$C_{15}$-carbocyclic group is a $C_3$-$C_{10}$-carbocyclic group, for example cyclopropyl, cyclopentyl, cyclohexyl, cycloheptyl, phenyl, indanyl or naphthyl. Phenyl is especially preferred. The $C_3$-$C_{15}$-carbocyclic group can be substituted or unsubstituted. Preferred substituents include halo e.g. fluoro, cyano, hydroxy, amino, nitro, carboxy, $C_1$-$C_{10}$-alkyl, $C_1$-$C_{10}$-haloalkyl, $C_1$-$C_{10}$-alkoxy, $C_1$-$C_{10}$-alkylcarbonyl, $C_1$-$C_{10}$-alkylsulfonyl, —$SO_2NH_2$, —COO—$C_6$-$C_{10}$-aryl, —COO—$C_7$-$C_{15}$-aralkyl, a $C_3$-$C_{15}$-carbocyclic group and a 5- to 12-membered heterocyclic group having at least one ring heteroatom selected from nitrogen, oxygen and sulphur. The "$C_3$-$C_{15}$-carbocyclic group" is most especially unsubstituted phenyl.

"$C_3$-$C_8$-cycloalkyl" as used herein denotes cycloalkyl having 3 to 8 carbon atoms. Preferably "$C_3$-$C_8$-cycloalkyl" is "$C_3$-$C_6$-cycloalkyl".

"$C_1$-$C_{10}$-haloalkyl" as used herein denotes $C_1$-$C_{10}$-alkyl as hereinbefore defined substituted by one or more halogen atoms, preferably one, two or three halogen atoms. Preferably "$C_1$-$C_{10}$-haloalkyl" is "$C_1$-$C_4$-haloalkyl".

"$C_1$-$C_{10}$-alkylcarbonyl" as used herein denotes $C_1$-$C_{10}$-alkyl as hereinbefore defined linked to a carbonyl group. Preferably "$C_1$-$C_{10}$-alkylcarbonyl" is "$C_1$-$C_4$-alkylcarbonyl".

"$C_1$-$C_{10}$-alkylsulfonyl" as used herein denotes $C_1$-$C_{10}$-alkyl as hereinbefore defined linked to —$SO_2$—. Preferably "$C_1$-$C_{10}$-alkylsulfonyl" is "$C_1$-$C_4$-alkylsulfonyl".

"15- to 12-membered heterocyclic group containing at least one ring heteroatom selected from nitrogen, oxygen and sulphur" as used herein denotes a monoheterocyclic, biheterocyclic or triheterocyclic group, which may be saturated or unsaturated, that has 5 to 12 ring atoms. Monoheterocyclic groups include furyl, pyrrolyl, pyrrolidinyl, pyrazolyl, imidazolyl, triazolyl, tetrazolyl, thienyl, thiadiazolyl, isothiazolyl, oxadiazolyl, pyridinyl, oxazolyl, isoxazolyl, piperidinyl, pyridinyl, pyrazinyl, pyridazinyl, pyrimidinyl, piperazinyl, morpholinyl, triazinyl, oxazinyl or thiazolyl. Biheterocyclic groups include benzazolyl, benzimidazolyl, indazolyl and benzothiazolyl. Preferably the 5- to 12-membered heterocyclic group is a 5- to 9-membered heterocyclic group. Preferred 5- to 9-membered heterocyclic groups include furyl, pyrrolyl, triazolyl, thienyl, thiadiazolyl, oxazolyl, isoxazolyl, piperidinyl, pyridinyl, pyrazinyl, benzazolyl, benzimidazolyl, indazolyl and benzothiazolyl, but especially thienyl. The 5- to 12-membered heterocyclic group can be unsubstituted or substituted, e.g. by one, two, three or four substituents. Preferred substituents include halo, cyano, oxo, hydroxy, carboxy, nitro, $C_1$-$C_{10}$-alkyl, $C_1$-$C_{10}$-alkylcarbonyl and $C_1$-$C_{10}$-alkoxy optionally substituted by aminocarbonyl.

"Aminocarbonyl" as used herein denotes amino attached through the nitrogen atom to a carbonyl group.

"$C_6$-$C_{10}$-aryl" as used herein denotes a monovalent carbocyclic aromatic group that contains 6 to 10 carbon atoms and which may be, for example, a monocyclic group such as phenyl or a bicyclic group such as naphthyl. Preferably $C_6$-$C_{10}$-aryl is $C_6$-$C_8$-aryl, especially phenyl.

"$C_7$-$C_{15}$-aralkyl" as used herein denotes alkyl, for example $C_1$-$C_5$-alkyl as hereinbefore defined, substituted by $C_6$-$C_{10}$-aryl as hereinbefore defined. Preferably $C_7$-$C_{15}$-aralkyl is $C_7$-$C_{10}$-aralkyl such as phenyl-$C_1$-$C_4$-alkyl.

Throughout this specification and in the claims that follow, unless the context requires otherwise, the word "comprise", or variations such as "comprises" or "comprising", will be understood to imply the inclusion of a stated integer or step or group of integers or steps but not the exclusion of any other integer or step or group of integers or steps.

Preferred compounds include those of formula I in salt or zwitterionic form where $R^1$ and $R^3$ are each independently a $C_3$-$C_{15}$-carbocyclic group or a 5- to 12-membered heterocyclic group having at least one ring heteroatom selected from nitrogen, oxygen and sulphur;
$R^2$ is hydroxy;
L and M are (a bond and —$CH_2$—$CH_2$—), (—$CH_2$— and —$CH_2$—$CH_2$—) or (—$CH_2$—$CH_2$— and —$CH_2$—) respectively and J is $C_1$-$C_2$-alkylene,
or L and M are (—$CH_2$— and —$CH_2$—$CH_2$—) or (—$CH_2$—$CH_2$— and —$CH_2$—) respectively and j is a bond;
$R^4$ is $C_1$-$C_4$-alkyl;
$R^5$ is $C_1$-alkyl substituted by —CO—$R^6$ or —CO—NH—$R^6$,
or $R^5$ is $C_2$-$C_{10}$-alkyl substituted by —O—$R^6$, —S—$R^6$, —O—CO—$R^6$ or —$R^8$,
or $R^5$ is $C_2$-$C_{10}$-alkenyl or $C_2$-$C_{10}$-alkynyl optionally substituted by —$R^8$;
$R^6$ is a $C_3$-$C_{15}$-carbocyclic group,
or $R^6$ is $C_1$-$C_{10}$-alkyl optionally substituted by $C_1$-$C_{10}$-alkoxy, O—$R^5$ or a $C_3$-$C_{15}$-carbocyclic group; and
$R^8$ is a $C_3$-$C_{15}$-carbocyclic group.

Especially preferred compounds include those of formula I in salt or zwitterionic form where $R^1$ and $R^3$ are each independently a $C_3$-$C_{10}$-carbocyclic group, preferably phenyl, or a 5- to 9-membered heterocyclic group having at least one ring heteroatom selected from nitrogen, oxygen and sulphur, preferably thienyl;
$R^2$ is hydroxy;
L and M are (a bond and —$CH_2$—$CH_2$—), (—$CH_2$— and —$CH_2$—$CH_2$—) or (—$CH_2$—$CH_2$— and —$CH_2$—) respectively and J is $C_1$-$C_2$-alkylene,
or L and M are (—$CH_2$— and —$CH_2$—$CH_2$—) or (—$CH_2$—$CH_2$— and —$CH_2$—) respectively and J is a bond;
$R^4$ is $C_1$-$C_4$-alkyl;
$R^5$ is $C_1$-alkyl substituted by —CO—$R^6$ or —CO—NH—$R^6$,
or $R^5$ is $C_2$-$C_5$-alkyl substituted by —O—$R^6$, —S—$R^6$, —O—CO—$R^6$ or —$R^8$,
or $R^5$ is $C_2$-$C_4$-alkenyl or $C_2$-$C_8$-alkynyl optionally substituted by —$R^8$;
$R^6$ is a $C_3$-$C_{10}$-carbocyclic group, preferably phenyl,
or $R^6$ is $C_1$-$C_{15}$-alkyl optionally substituted by $C_1$-$C_4$-alkoxy, O—$R^8$ or a $C_3$-$C_{10}$-carbocyclic group; and
$R^8$ is a $C_3$-$C_{10}$-carbocyclic group, preferably phenyl.

In a second aspect the invention provides compounds of formula Ia

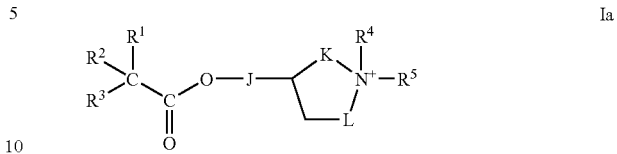

in salt or zwitterionic form wherein $R^1$ and $R^3$ are each independently a $C_3$-$C_{15}$-carbocyclic group or a 5- to 12-membered heterocyclic group having at least one ring heteroatom selected from nitrogen, oxygen and sulphur;
$R^2$ is hydrogen, hydroxy, or $C_1$-$C_4$-alkyl optionally substituted by hydroxy;
J and K are both independently $C_1$-$C_2$-alkylene,
or one of J and K is a bond and the other is $C_1$-$C_2$-alkylene;
L is $C_1$-$C_2$-alkylene;
$R^4$ is $C_1$-$C_4$-alkyl;
$R^5$ is $C_1$-$C_8$-alkyl substituted by —$OR^6$, —O—CO—$R^6$ or —CO—O—$R^6$; and
$R^6$ is $C_1$-$C_8$-alkyl, a $C_3$-$C_{15}$-carbocyclic group or a 5- to 12-membered heterocyclic group having at least one ring heteroatom selected from nitrogen, oxygen and sulphur.

Preferred compounds also include those of formula Ia in salt or zwitterionic form where $R^1$ and $R^3$ are each independently a $C_3$-$C_{15}$-carbocyclic group;
$R^2$ is hydroxy;
J is a bond;
K is $C_1$-$C_2$-alkylene;
L is $C_1$-$C_2$-alkylene;
$R^4$ is $C_1$-$C_4$-alkyl;
$R^5$ is $C_1$-$C_8$-alkyl substituted by —$OR^6$; and
$R^6$ is a $C_3$-$C_{15}$-carbocyclic group.

Especially preferred compounds also include those of formula Ia in salt or zwitterionic form where $R^1$ and $R^3$ are each independently a $C_3$-$C_{10}$-carbocyclic group, preferably phenyl;
$R^2$ is hydroxy;
J is a bond;
K is $C_1$-$C_2$-alkylene;
L is $C_1$-$C_2$-alkylene;
$R^4$ is methyl;
$R^5$ is $C_1$-$C_4$-alkyl substituted by —$OR^6$; and
$R^6$ is a $C_3$-$C_{10}$-carbocyclic group, preferably phenyl.

The compounds of formula I are quaternary ammonium salts. Suitable counter ions are pharmaceutically acceptable counter ions including, for example, fluoride, chloride, bromide, iodide, nitrate, sulfate, phosphate, formate, acetate, trifluoroacetate, propionate, butyrate, lactate, citrate, tartrate, malate, maleate, succinate, benzoate, p-chlorobenzoate, diphenyl-acetate or triphenylacetate, o-hydroxybenzoate, p-hydroxybenzoate, 1-hydroxynaphthalene-2-carboxylate, 3-hydroxynaphthalene-2-carboxylate, methanesulfonate and benzenesulfonate.

Compounds of formula I that contain a basic centre are capable of forming acid addition salts, particularly pharmaceutically acceptable acid addition salts. Pharmaceutically acceptable acid addition salts of the compound of formula I include those of inorganic acids, for example, hydrohalic acids such as hydrofluoric acid, hydrochloric acid, hydrobromic acid or hydroiodic acid, nitric acid, sulfuric acid, phosphoric acid; and organic acids, for example aliphatic monocarboxylic acids such as formic acid, acetic acid, trifluoroacetic acid, propionic acid and butyric acid, aliphatic hydroxy acids such as lactic acid, citric acid, tartaric acid or malic acid, dicarboxylic acids such as maleic acid or succinic acid, aromatic carboxylic acids such as benzoic acid, p-chlorobenzoic acid, diphenylacetic acid or triphenylacetic acid, aromatic hydroxy acids such as o-hydroxybenzoic acid, p-hydroxybenzoic acid, 1-hydroxynaphthalene-2-carboxylic acid or 3-hydroxynaphthalene-2-carboxylic acid, and sulfonic acids such as methanesulfonic acid or benzenesulfonic acid. These salts may be prepared from compounds of formula I by known salt-forming procedures.

Compounds of formula I which contain acidic e.g. carboxyl groups, are also capable of forming salts with bases, in particular pharmaceutically acceptable bases such as those well known in the art; suitable such salts include metal salts, particularly alkali metal or alkaline earth metal salts such as sodium, potassium, magnesium or calcium salts, or salts with ammonia or pharmaceutically acceptable organic amines or heterocyclic bases such as ethanolamines, benzylamines or pyridine. These salts may be prepared from compounds of formula I by known salt-forming procedures.

In those compounds where there is one or more chiral centre the compounds exist in individual optically active isomeric forms or as mixtures thereof, e.g. as racemic or diastereomeric mixtures. For example in those compounds wherein the moiety represented by J creates a chiral centre at the attached ring carbon atom, the quaternary nitrogen atom is also a chiral centre and hence four possible diastereoisomers exist. The present invention embraces both individual optically active R and S isomers as well as mixtures, e.g. racemic or diastereomeric mixtures, thereof. Particularly preferred compounds of in invention are single isomers, either single enantiomers or single diastereoisomers. Surprisingly these single isomers allow the most potent component of a mixture to be selected and surprisingly can offer improved residency times at the M3 receptor hence delivering agents with long duration of action which are particularly suitable for once-daily dosing.

Specific especially preferred compounds of the invention are those described hereinafter in the Examples.

The invention also provides a process for the preparation of compounds of formula I which comprises:

(i) (A) reacting a compound of formula II

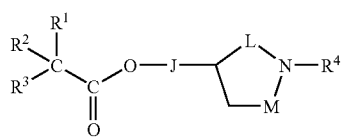

or a protected form thereof where $R^1$, $R^2$, $R^3$, $R^4$, J, L and M are as hereinbefore defined, with a compound of formula III $$X—R^5 \qquad \qquad III$$

where $R^5$ is as hereinbefore defined and X is chloro, bromo or iodo;

(B) reacting a compound of formula IV

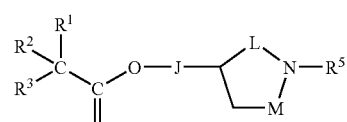

or a protected form thereof where $R^1$, $R^2$, $R^3$, $R^5$, J, L and M are as hereinbefore defined, with a compound of formula V $$X—R^4 \qquad \qquad V$$

where $R^4$ is as hereinbefore defined and X is chloro, bromo or iodo;

(C) for the preparation of compounds of formula I where $R^5$ is -Q-NH—CO—$R^6$, reacting a compound of formula VI

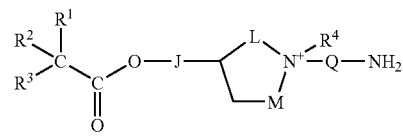

or a protected form thereof where $R^1$, $R^2$, $R^3$, $R^4$, J, L and M are as hereinbefore defined and Q is $C_1$-$C_{10}$-alkylene, with a compound of formula VII

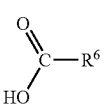

or an amide-forming derivative thereof wherein $R^6$ is as hereinbefore defined; or (D) for the preparation of compounds of formula I where $R^5$ is $C_1$-$C_{10}$-alkyl substituted by a $C_3$-$C_{15}$-carbocyclic group that is substituted by carboxy, converting a compound of formula I where $R^1$, $R^2$, $R^3$, $R^4$, J, L and M are as hereinbefore defined and $R^5$ is $C_1$-$C_{10}$-alkyl substituted by a $C_3$-$C_{15}$-carbocyclic group that is substituted by either —COO—$C_6$-$C_{10}$-aryl or —COO—$C_7$-$C_{15}$-aralkyl; and (ii) recovering the product in salt or zwitterionic form.

Process variant (A) may be effected using known procedures for reacting saturated heterocyclic amines with halogenides or analogously as hereinafter described in the Examples. The reaction is conveniently carried out in an organic solvent, for example dimethylsulphoxide, dimethylformamide, ether, acetonitrile or acetone. The reaction is carried out at a temperature between 20° C. to 120° C., conveniently between room temperature and 80° C.

Process variant (B) may be effected using known procedures for reacting saturated heterocyclic amines with halogenides or analogously as hereinafter described in the Examples. The reaction is conveniently carried out in an organic solvent, for example dimethylsulphoxide, dimethylformamide, ether, acetonitrile or acetone. The reaction is carried out at a temperature between 20° C. to 120° C., conveniently between room temperature and 80° C.

Process variant (C) may be carried out using known procedures for reacting carboxylic acids (or amide-forming derivatives thereof such as acid halide derivatives) with amines, or analogously e.g. as hereinafter described in the Examples. The reaction is conveniently carried out by reacting the carboxylic acid with the amine using an organic solvent, for example dimethylformamide, in the presence of one or more coupling agents, for example O-(7-azabenzotriazol-1-yl)-1,1,3-,3-tetramethyluronium hexafluoro-phosphate (HATU), and a base, for example diisopropylethylamine (DIPEA). Suitable reaction temperatures are from 10° C. to 40° C., for example room temperature.

Process variant (D) may be effected using known procedures for converting esters to form the corresponding carboxylic acids, or analogously as hereinafter described in the Examples. The reaction may be conveniently carried out by catalytic hydrogenation, e.g. with Palladium on Carbon 10%, e.g. in an organic solvent, such as dimethylformamide. The reaction is conveniently carried out at room temperature.

When a compound of formula II is a single enantiomer or is achiral, alkylation of the tertiary amine to give a compound of formula I results in a mixture of two diastereoisomers. These isomers may be separated by conventional techniques, e.g. by fractional crystallization or column chromatography.

Compounds of formula II may exist in individual optically active isomeric forms or as mixtures thereof, e.g. as racemic or diastereomeric mixtures. Preferred compounds of formula II are compounds of formula IIa or IIb

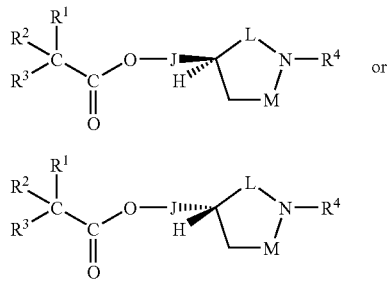

IIa

IIb or a protected form thereof where $R^1$, $R^2$, $R^3$, $R^4$, J, L and M are as herein before defined.

Compounds of formula II are known or may be prepared by reacting a compound of formula VIII

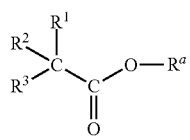

VIII or a protected form thereof where $R^1$, $R^2$ and $R^3$ are as hereinbefore defined and $R^a$ is $C_1$-$C_4$-alkyl, with a compound of formula IX

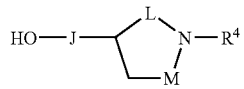

IX where $R^4$, J, L and M are as hereinbefore defined. The reaction may be effected using known procedures for reacting carboxylic esters with alcohols or analogously as hereinafter described in the Examples. The reaction is conveniently carried out in an organic solvent, for example cyclohexane or toluene, preferably in the presence of an alkali metal e.g. sodium and under an inert atmosphere such as argon. The reaction may be carried out at a temperature between 40° C. to 120° C., but preferably under reflux conditions.

Compounds of formula II where $R^2$ is hydroxyl may be prepared by reacting a compound of formula X

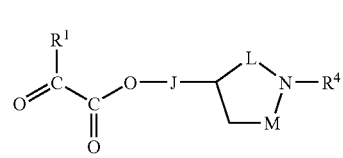

X or a protected form thereof where $R^1$, $R^4$, J, L and M are as hereinbefore defined, with a compound of formula XI

XI where $R^3$ is as hereinbefore defined and X is chloro, bromo or iodo.

Compounds of formula m are known or may be prepared by known procedures, or analogously as hereinafter described in the Examples.

Compounds of formula IV may exist in individual optically active isomeric forms or as mixtures thereof, e.g. as racemic or diastereomeric mixtures. Preferred compounds of formula IV are compounds of formula IVa or IVb

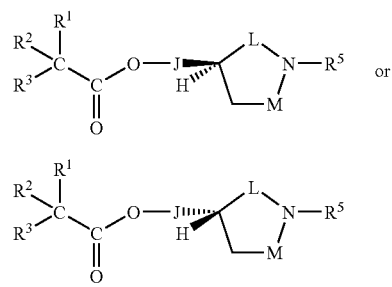

IVa

IVb or a protected form thereof where $R^1$, $R^2$, $R^3$, $R^5$, J, L and M are as hereinbefore defined.

Compounds of formula IV may be prepared by reacting a compound of formula VIII or a protected form thereof where $R^1$, $R^2$ and $R^3$ are as hereinbefore defined and $R^a$ is $C_1$-$C_4$-alkyl, with a compound of formula XII

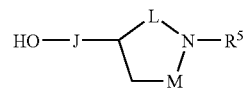

XII where $R^5$, J, L and M are as hereinbefore defined. The reaction may be effected using known procedures for reacting carboxylic esters with alcohols or analogously as hereinafter described in the Examples. The reaction is conveniently carried out in an organic solvent, for example cyclohexane or toluene, preferably in the presence of an alkali metal e.g.

sodium and under an inert atmosphere such as argon. The reaction may be carried out at a temperature between 40° C. to 120° C., but preferably under reflux conditions.

Compounds of formula V are known or may be prepared by known procedures, or analogously as hereinafter described in the Examples.

Compounds of formula VI are novel and may be prepared by reacting a compound of formula II where $R^1$, $R^2$, $R^3$, $R^4$, J, M and L are as hereinbefore defined, with a compound of formula XIII

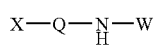

XIII where X is chloro, bromo or iodo, Q is $C_1$-$C_{10}$-alkylene and W is a protecting group. This reaction may be effected using known procedures for reacting heterocyclic amines with haloalkylamines, or analogously as hereinafter described in the Examples. The reaction is conveniently carried out in an organic solvent, for example dimethylformamide. The reaction may be carried out at a temperature between 40° C. to 80° C., preferably between 50° C. to 70° C., but especially about 60° C. The protecting group is preferably a tert-butoxycarbonyl group.

Compounds of formula VII or VIII are known or may be prepared by known procedures, or analogously as hereinafter described in the Examples.

Compounds of formula IX and XII are known or may be prepared by alkylating the corresponding secondary amine. For example compounds of formula IX where $R^4$ is methyl may be prepared by reacting a compound of formula XIV

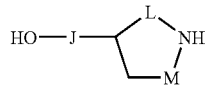

XIV where J, L and M are as hereinbefore defined with formaldehyde in the presence of formic acid. The reaction is conveniently carried out in a solvent, for example water, at a temperature from 40° C. to 120° C., but preferably about 80° C. Alternatively, compounds of formula X may be prepared by reacting a compound of formula XII where J, L and M are as hereinbefore defined with a compound of formula III where $R^5$ is as hereinbefore defined and X is chloro, bromo or iodo. The reaction is conveniently carried out in an organic solvent, for example acetonitrile, at a temperature from 40° C. to 120° C., but preferably under reflux in the presence of base, for example potassium carbonate.

Compounds of formula X may be prepared by reacting a compound of formula IX where $R^4$, J, L and M are as hereinbefore defined, with a compound of formula XV

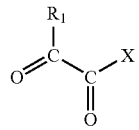

XV where $R^1$ is as hereinbefore defined and X is chloro, bromo or iodo.

Compounds of formula XI, XIB, XIV or XV are known or may be prepared by known procedures, or analogously as hereinafter described in the Examples.

Where reference is made herein to protected functional groups or to protecting groups, the protecting groups may be chosen in accordance with the nature of the functional group, for example as described in Protective Groups in Organic Synthesis, T. W. Greene and P. G. M. Wuts, John Wiley & Sons Inc, Third Edition, 1999, which reference also describes procedures suitable for replacement of the protecting groups by hydrogen.

Compounds of formula I are quaternary ammonium salts and may be converted between different salt forms using ion exchange chromatography. The compounds can be obtained in the form of hydrates or solvates containing a solvent used for crystallization. Compounds of formula I can be recovered from reaction mixtures and purified using known methods. The compounds are initially isolated as diastereomeric mixtures however in most cases they are preferably used in pharmaceutical compositions of the invention as single enantiomers or diastereoisomers.

Compounds of formula I in pharmaceutically acceptable salt or zwitterionic form, hereinafter referred to alternatively as agents of the invention, are useful as pharmaceuticals. Accordingly the invention also provides a compound of formula I in pharmaceutically acceptable salt or zwitterionic form for use as a pharmaceutical. The agents of the invention act as muscarinic antagonists, particularly muscarinic M3 receptor antagonists thereby acting as inhibitors of bronchoconstriction.

The affinity (Ki) of agents of the invention at the human muscarinic acetylcholine M3 receptor can be determined in a competitive filtration binding assay with the radio-labelled antagonist [$^3$H] n-methyl scopolamine methyl chloride (NMS):

Membranes prepared from CHO cells stably are transfected with human M3 receptor at 10 µg protein/well then incubated with serial dilutions of the agents of the invention, [$^3$H]NMS at Kd concentration (0.25 nM) and assay buffer (20 mmol HEPES, 1 mmol $MgCl_2$ at pH 7.4) for 17 hours at room temperature. The assay is carried out in a 250 µL final volume, in the presence of a final dimethyl sulfoxide concentration of 1%. Total binding of [$^3$H]NMS is determined in the absence of the agents of the invention with a corresponding substituted volume of assay buffer. Non-specific binding of [$^3$H] NMS is determined in the presence of 300 nM ipratropium bromide. Following the incubation period, the membranes are harvested onto a Unifilter™ GF/B filter plate containing 0.05% polyethyleneimine, using a Brandel™ filtration harvester 9600. Filter plates are dried for two hours at 35° C. before the addition of Microscin™ 'O' cocktail, and are read on a Packard Topcount™ scintillator using a $^3$H-Scintillation protocol. All IC50s are calculated with the aid of XL-Fit graph package and $K_i$ values are derived using the Cheng-Prusoff correction (Cheng Y., Prusoff W. H. (1973) *Biochem. Pharmacol.* 22 3099-3109).

The compounds of the Examples hereinbelow generally have $IC_{50}$ values below 1 µM in the above assay. For instance, the compounds of Examples 1a, 1b, 2, 13, 25, 29, 46b, 47b, 49, 63, 88, 95, 96a and 97b have M3 $K_i$ values of 1.4, 1.3, 2.14, 0.39, 3.7, 0.41, 0.64, 0.55, 0.68, 0.33, 0.88, 0.44, 0.2 and 0.75 nM respectively.

Having regard to their inhibition of acetyl choline binding to M3 muscarinic receptors, agents of the invention are useful in the treatment of conditions mediated by the muscarinic M3 receptor, particularly those associated with increased parasympathetic tone leading to, for example, excessive glandular secretion or smooth muscle contraction. Treatment in accordance with the invention may be symptomatic or prophylactic.

Having regard to their antimuscarinic activity, the agents of the invention are useful in the relaxation of bronchial smooth muscle and the relief of bronchoconstriction. Relief of bronchoconstriction can be measured in models such as the in vivo plethysmography models of Chong et al, *J. Pharmacol. Toxicol. Methods* 1998, 39, 163, Hammelmann et al, *Am. J. Respir. Crit. Care Med.*, 1997, 156, 766 and analogous models. The agents of the invention are therefore useful in the treatment of obstructive or inflammatory airways diseases. In view of their long duration of action, it is possible to administer the agents of the invention once-a-day in the treatment of such diseases. In another aspect, agents of the invention commonly exhibit characteristics indicating a low incidence of side effects commonly encountered with $\beta_2$ agonists such as tachycardia, tremor and restlessness, such agents accordingly being suitable for use in on demand (rescue) treatment as well as prophylactic treatment of obstructive or inflammatory airways diseases.

Inflammatory or obstructive airways diseases to which the present invention is applicable include asthma of whatever type or genesis including both intrinsic (non-allergic) asthma and extrinsic (allergic) asthma. Treatment of asthma is also to be understood as embracing treatment of subjects, e.g. of less than 4 or 5 years of age, exhibiting wheezing symptoms and diagnosed or diagnosable as "wheezy infants", an established patient category of major medical concern and now often identified as incipient or early-phase asthmatics. (For convenience this particular asthmatic condition is referred to as "wheezy-infant syndrome".)

Prophylactic efficacy in the treatment of asthma will be evidenced by reduced frequency or severity of symptomatic attack, e.g. of acute asthmatic or bronchoconstrictor attack, improvement in lung function or improved airways hyperreactivity. It may further be evidenced by reduced requirement for other, symptomatic therapy, i.e. therapy for or intended to restrict or abort symptomatic attack when it occurs, for example anti-inflammatory (e.g. corticosteroid) or bronchodilatory. Prophylactic benefit in asthma may in particular be apparent in subjects prone to "morning dipping". "Morning dipping" is a recognised asthmatic syndrome, common to a substantial percentage of asthmatics and characterised by asthma attack, e.g. between the hours of about 4 to 6 am, i.e. at a time normally substantially distant from any previously administered symptomatic asthma therapy.

Other inflammatory or obstructive airways diseases and conditions to which the present invention is applicable include adult/acute respiratory distress syndrome (ARDS), chronic obstructive pulmonary or airways disease (COPD or COAD), including chronic bronchitis, or dyspnea associated therewith, emphysema, as well as exacerbation of airways hyperreactivity consequent to other drug therapy, in particular other inhaled drug therapy. The invention is also applicable to the treatment of bronchitis of whatever type or genesis including, e.g., acute, arachidic, catarrhal, croupus, chronic or phthinoid bronchitis. Further inflammatory or obstructive airways diseases to which the present invention is applicable include pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, cystic fibrosis, ptilosis, siderosis, silicosis, tabacosis and byssinosis.

Having regard to their antimuscarinic activity, the agents of the invention are also useful in the treatment of a condition requiring relaxation of smooth muscle of the uterus, bladder or vascular system. They are thus useful for the prevention or alleviation of premature labour pains in pregnancy. They are also useful in the treatment of chronic and acute urticaria, psoriasis, allergic conjunctivitis, actinitis, rhinitis including allergic rhinitis, mastocytosis, urinary disorders such as urinary incontinence (particularly that caused by an overactive bladder), pollakiuria, neurogenic or unstable bladder, cystospasm and chronic cystitis; gastrointestinal disorders such as irritable bowel syndrome, spastic colitis, diverticulitis and peptic ulceration; and cardiovascular disorders such as vagally induced sinus bradycardia, as well as in ophthalmic interventions.

The agents of the invention are also useful as co-therapeutic agents for use in combination with other drug substances such as anti-inflammatory, bronchodilatory, antihistamine, decongestant or anti-tussive drug substances, particularly in the treatment of obstructive or inflammatory airways diseases such as those mentioned hereinbefore, for example as potentiators of therapeutic activity of such drugs or as a means of reducing required dosaging or potential side effects of such drugs. An agent of the invention may be mixed with one or more the other drug substances in a fixed pharmaceutical composition or it may be administered separately, before, simultaneously with or after the other drug substance(s). Accordingly the invention includes a combination of an agent of the invention as hereinbefore described with an anti-inflammatory, bronchodilatory, antihistamine, decongestant or anti-tussive drug substance, said agent of the invention and said drug substance being in the same or different pharmaceutical composition.

Such anti-inflammatory drugs include steroids, for example glucocorticosteroids such as budesonide, beclamethasone, fluticasone, ciclesonide or mometasone, or steroids described in WO 02/88167, WO 02/12266, WO 02/100879 or WO 02/00679, especially those of Examples 3, 11, 14, 17, 19, 26, 34, 37, 39, 51, 60, 67, 72, 73, 90, 99 and 101, and non-steroidal steroid agonists such as those described in WO 00/00531, WO 02/10143, WO 03/082280, WO 03/082787, WO 03/104195, WO 04/005229; LTB4 antagonists such as those described in U.S. Pat. No. 5,451, 700, also LY293111, CGS025019C, CP-195543, SC-53228, BIIL 284, ONO 4057, SB 209247; LTD4 antagonists such as montelukast and zafirlukast; PDE4 inhibitors such as cilomilast (Ariflo® GlaxoSmithKline), Roflumilast (Byk Gulden), V-11294A (Napp), BAY19-8004 (Bayer), SCH-351591 (Schering-Plough), Arofylline (Almirall Prodesfarma), PD189659 (Parke-Davis), AWD-12-281 (Asta Medica), CDC-801 (Celgene), SelCID™ CC-10004 (Celgene), KW-4490 (Kyowa Hakko Kogyo), WO 03/104204, WO 03/104205, WO 04/000814, WO 04/000839 and WO 04005258 (Merck), as well as those described in WO 98/18796 and WO 03/39544; A2a agonists such as those described in EP 1052264, EP 1241176, EP 409595A2, WO 94/17090, WO 96/02543, WO 96/02553, WO 98/28319, WO 99/24449, WO 99/24450, WO 99/24451, WO 99/38877, WO 99/41267, WO 99/67263, WO 99/67264, WO 99/67265, WO 99/67266, WO 00/23457, WO 00/77018, WO 00/78774, WO 01/23399, WO 01/27130, WO 01/27131, WO 01/60835, WO 01/94368, WO 02/00676, WO 02/22630, WO 02/96462, and WO 03/086408; and A2b antagonists such as those described in WO 02/42298.

The agents of the invention are useful in combination therapy with chemokine receptor antagonists, calcium channel blockers, alpha-adrenoceptor antagonists, dopamine agonists, endothelin antagonists, substance-P antagonists, 5-LO inhibitors, VLA-4 antagonists and theophylline.

The agents of the invention are also particularly useful as co-therapeutic agents for use in combination with beta-2 adrenoceptor agonists or corticosteroids. Suitable beta-2 adrenoceptor agonists include salbutamol, terbutaline, salmeterol and, especially, formoterol and pharmaceutically acceptable salts thereof, and compounds (in free or salt or solvate form) of formula I of WO 0075114, which document is incorporated herein by reference, preferably compounds of the Examples thereof, especially a compound of formula

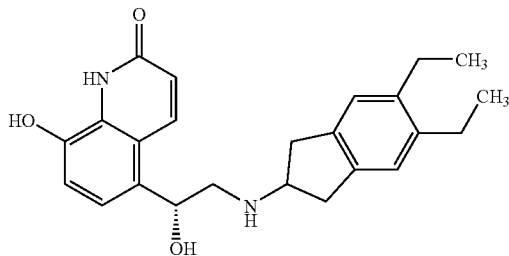

and pharmaceutically acceptable salts thereof, as well as compounds (in free or salt or solvate form) of formula I of WO 04/16601, preferably the compounds of Examples 1, 3, 4, 5 and 79.

Co-therapeutic antihistamine drug substances include cetirizine hydrochloride, acetaminophen, clemastine fumarate, promethazine, loratidine, desloratidine, diphenhydramine and fexofenadine hydrochloride, activastine, astemizole, azelastine, ebastine, epinastine, mizolastine and tefenadine.

Combinations of agents of the invention and one or more of beta-2 adrenoceptor agonists, steroids, PDE4 inhibitors, A2a agonists, A2b antagonists and LTD4 antagonists may be used, for example, in the treatment of airways diseases, including asthma and particularly COPD. Preferred triple combinations comprise an agent of the invention, a beta-2 adrenoceptor agonist and a steroid.

In accordance with the foregoing, the present invention also provides a method for the treatment of an obstructive or inflammatory airways disease which comprises administering to a subject, particularly a human subject, in need thereof a compound of formula I, or a pharmaceutically acceptable salt or solvate thereof, as hereinbefore described. In another aspect, the invention provides a compound of formula I, or a pharmaceutically acceptable salt or solvate thereof, as hereinbefore described for use in the preparation of a medicament for the treatment of an obstructive or inflammatory airways disease.

The agents of the invention may be administered by any appropriate route, e.g. orally, for example in the form of a tablet or capsule; parenterally, for example intravenously; topically to the skin, for example in the treatment of psoriasis; intranasally, for example in the treatment of hay fever; or, preferably, by inhalation, particularly in the treatment of obstructive or inflammatory airways diseases. In particular, the agents of the invention may be delivered as an inhalable formulation for the treatment of COPD and asthma.

In a further aspect, the invention also provides a pharmaceutical composition comprising a compound of formula I in free form or in the form of a pharmaceutically acceptable salt or solvate thereof, optionally together with a pharmaceutically acceptable diluent or carrier therefor. Such compositions may be prepared using conventional diluents or excipients and techniques known in the galenic art. Thus oral dosage forms may include tablets and capsules. Formulations for topical administration may take the form of creams, ointments, gels or transdermal delivery systems, e.g. patches. Compositions for inhalation may comprise aerosol or other atomizable formulations or dry powder formulations.

When the composition comprises an aerosol formulation, it preferably contains, for example, a hydro-fluoro-alkane (HFA) propellant such as HFA134a or HFA227 or a mixture of these, and may contain one or more co-solvents known in the art such as ethanol (up to 20% by weight), and/or one or more surfactants such as oleic acid or sorbitan trioleate, and/or one or more bulking agents such as lactose. When the composition comprises a dry powder formulation, it preferably contains, for example, the compound of formula I having a particle diameter up to 10 microns, optionally together with a diluent or carrier, such as lactose, of the desired particle size distribution and a compound that helps to protect against product performance deterioration due to moisture e.g. magnesium stearate. When the composition comprises a nebulised formulation, it preferably contains, for example, the compound of formula I either dissolved, or suspended, in a vehicle containing water, a co-solvent such as ethanol or propylene glycol and a stabiliser, which may be a surfactant.

The invention also includes (A) a compound of formula I as hereinbefore described in free form, or a pharmaceutically acceptable salt or solvate thereof, in inhalable form; (B) an inhalable medicament comprising such a compound in inhalable form together with a pharmaceutically acceptable carrier in inhalable form; (C) a pharmaceutical product comprising such a compound in inhalable form in association with an inhalation device; and (D) an inhalation device containing such a compound in inhalable form.

Dosages of agents of the invention employed in practising the present invention will of course vary depending, for example, on the particular condition to be treated, the effect desired and the mode of administration. In general, suitable daily dosages for administration by inhalation are of the order of 0.0001 to 30 mg/kg, typically 0.01 to 10 mg per patient, while for oral administration suitable daily doses are of the order of 0.01 to 100 mg/kg.

The invention is illustrated by the following Examples.

EXAMPLES

All compounds of these examples are initially isolated as mixtures of diastereoisomers at the quaternary nitrogen atom. Where an individual diastereoisomer is indicated in these examples it is isolated by fractional crystallisation of such a mixture. The stereochemistry of these single isomers is determined by nmr and/or xray crystallography.

Especially preferred compounds of formula I include compounds of formula XVI

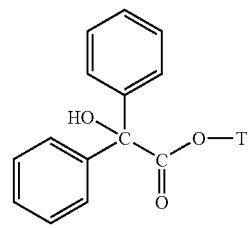

XVI where T is as shown in Table 1 below, the method of preparation being described hereinafter. All compounds are quaternary ammonium salts. The table also shows mass spectrometry data. The relevant counterion is identified in the relevant method of preparation.

TABLE 1

| Ex. | T | M/s M+ |
|---|---|---|
| 1a | [structure] | 446.32 |
| 1b | [structure] | 446.27 |

Further especially preferred compounds of formula I are compounds of formula XVI where T is as shown in Tables 2 and 3 below, the methods of preparation being described hereinafter. All compounds are quaternary ammonium salts. The tables also show mass spectrometry data. The relevant counterion is identified in the relevant method of preparation.

TABLE 2

| Ex. | T | M/s M+ |
|---|---|---|
| 2 | [structure] | 434.34 |
| 3 | [structure] | 460.35 |
| 4 | [structure] | 460.33 |
| 5 | [structure] | 442.31 |
| 6 | [structure] | 430.32 |
| 7 | [structure] | 444.33 |
| 8 | [structure] | 380.29 |
| 9 | [structure] | 364.25 |
| 10 | [structure] | 398.31 |
| 11 | [structure] | 428.34 |
| 12 | [structure] | 460.36 |
| 13 | [structure] | 430.32 |
| 14 | [structure] | 444.34 |
| 15 | [structure] | 460.39 |
| 16 | [structure] | 446.36 |
| 17 | [structure] | 442.36 |
| 18 | [structure] | 444.34 |

TABLE 2-continued
| Ex. | T | M/s M+ |
|---|---|---|
| 19 | 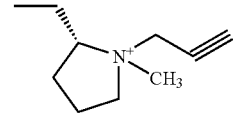 | 364.3 |
| 20 | 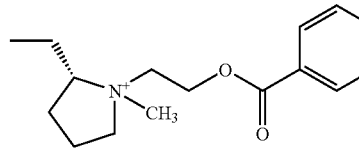 | 474.37 |
| 21 | 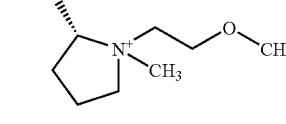 | 384.39 |
| 22 | 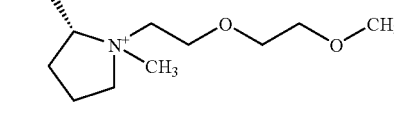 | 428.36 |
| 23 | 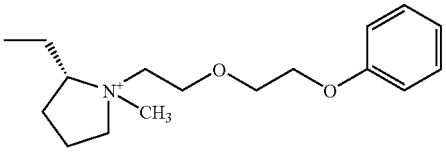 | 490.39 |
| 24 | 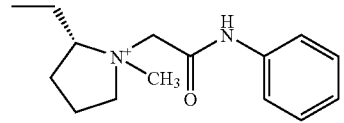 | 459.33 |
TABLE 3
| Ex. | T | M/s M+ |
|---|---|---|
| 25 |  | 458.34 |
| 26 | 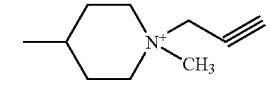 | 430.1 |
| 27 | 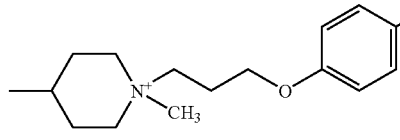 | 460.33 |
| 28 | 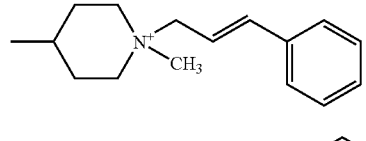 | 444.34 |
| 29 | 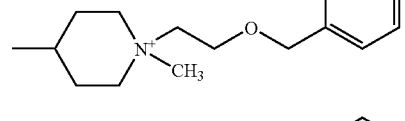 | 364.25 |
| 30 | 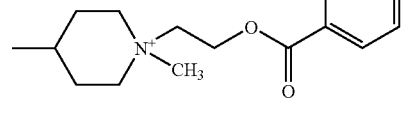 | 478.34 |
| 31 | 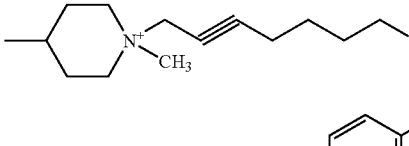 | 442.32 |
| 32 | 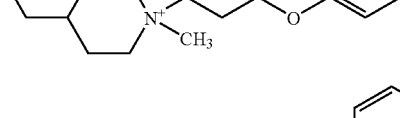 | 460.4 |
| 33 | 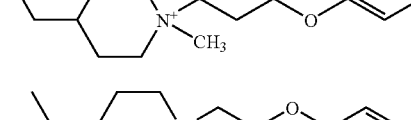 | 474.34 |
| 34 | 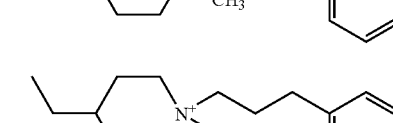 | 434.35 |
| 35 | 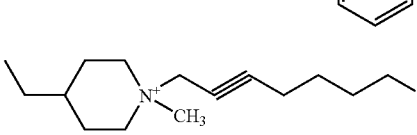 | 492.36 |
| 36 |  | 474.37 |
| 37 | | 460.35 |
| 38 | | 458.37 |
| 39 | | 448.38 |

TABLE 3-continued

| Ex. | T | M/s M+ |
|---|---|---|
| 40 | 4-ethyl-1-methylpiperidinium with 2-(phenylthio)ethyl | 476.36 |
| 41 | 4-ethyl-1-methylpiperidinium with 2-phenylethyl | 444.36 |
| 42 | 4-methyl-1-methylpiperidinium with CH2C(O)NHPh | 459.24 |
| 43 | 4-methyl-1-methylpiperidinium with 3-phenoxypropyl | 460.26 |
| 44 | 4-methyl-1-methylpiperidinium with 3-phenoxypropyl | 460.23 |
| 45 | 4-methyl-1-methylpiperidinium with 2-(4-(benzyloxycarbonyl)phenyl)ethyl | 564.34 |
| 46a | (3-methylpiperidinium) with 2-phenoxyethyl | 446.19 |
| 46b | (3-methylpiperidinium) with 2-phenoxyethyl | 446.1 |
| 46c | (3-methylpiperidinium) with 2-phenoxyethyl | 446.19 |
| 47a | (3-methylpiperidinium) with 3-phenylpropyl | 444.2 |

TABLE 3-continued

| Ex. | T | M/s M+ |
|---|---|---|
| 47b | (3-methylpiperidinium) with 3-phenylpropyl | 444.2 |
| 48 | (3-methylpiperidinium) with 3-phenoxypropyl | 460.3 |

Yet further especially preferred compounds of formula I include compounds of formula XVII

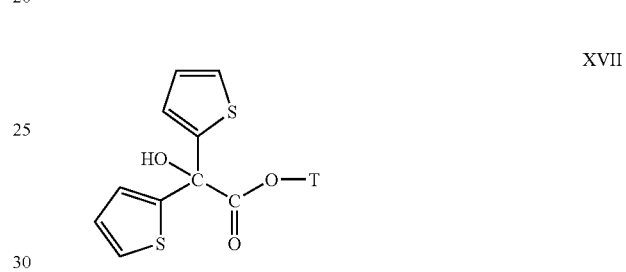

XVII where T is as shown in Tables 4 and 5 below, the methods of preparation being described hereinafter. AR compounds are quaternary ammonium salts. The tables also show mass spectrometry data. The relevant counterion is identified in the relevant method of preparation.

TABLE 4

| Ex. | T | M/s M+ |
|---|---|---|
| 49 | 2-ethyl-1-methylpyrrolidinium with 3-phenoxypropyl | 472.29 |
| 50 | 2-ethyl-1-methylpyrrolidinium with 2-phenoxyethyl | 458.27 |
| 51 | 2-ethyl-1-methylpyrrolidinium with 2-benzyloxyethyl | 472.29 |
| 52 | 2-ethyl-1-methylpyrrolidinium with 2-phenylethyl | 442.26 |

TABLE 4-continued

| Ex. | T | M/s M+ |
|---|---|---|
| 53 | (2-ethyl-1-methylpyrrolidinium, N-(3-phenylpropyl)) | 456.29 |
| 54 | (2-ethyl-1-methylpyrrolidinium, N-(phenacyl)) | 456.24 |
| 55 | (2-ethyl-1-methylpyrrolidinium, N-(propargyl)) | 376.20 |
| 56 | (2-ethyl-1-methylpyrrolidinium, N-(oct-2-ynyl)) | 446.29 |
| 57 | (2-ethyl-1-methylpyrrolidinium, N-(2-acetoxyethyl)) | 424.25 |
| 58 | (2-ethyl-1-methylpyrrolidinium, N-(2-benzoyloxyethyl)) | 486.27 |
| 59 | (2-ethyl-1-methylpyrrolidinium, N-(but-3-enyl)) | 392.23 |
| 60 | (2-ethyl-1-methylpyrrolidinium, N-(2-methoxyethyl)) | 396.23 |
| 61 | (2-ethyl-1-methylpyrrolidinium, N-(2-ethoxyethyl)) | 410.25 |
| 62 | (2-ethyl-1-methylpyrrolidinium, N-(2-(2-methoxyethoxy)ethyl)) | 440.26 |

TABLE 5

| Ex. | T | M/s M+ |
|---|---|---|
| 63 | (4-methyl-1-methylpiperidinium, N-(propargyl)) | 376.2 |
| 64 | (4-methyl-1-methylpiperidinium, N-(2-phenylethyl)) | 442.27 |
| 65 | (4-methyl-1-methylpiperidinium, N-(3-phenoxypropyl)) | 472.29 |
| 66 | (4-methyl-1-methylpiperidinium, N-(2-methoxyethyl)) | 396.22 |
| 67 | (4-methyl-1-methylpiperidinium, N-(3-phenylpropyl)) | 456.29 |
| 68 | (4-methyl-1-methylpiperidinium, N-(2-(2-methoxyethoxy)ethyl)) | 440.27 |
| 69 | (4-methyl-1-methylpiperidinium, N-(2-methoxyethyl)) | 410.24 |
| 70 | (4-methyl-1-methylpiperidinium, N-(cinnamyl)) | 454.27 |
| 71 | (4-methyl-1-methylpiperidinium, N-(3-(4-fluorophenoxy)propyl)) | 490.29 |
| 72 | (4-methyl-1-methylpiperidinium, N-(2-acetoxyethyl)) | 424.23 |
| 73 | (4-methyl-1-methylpiperidinium, N-(2-benzyloxyethyl)) | 472.28 |
| 74 | (4-methyl-1-methylpiperidinium, N-(2-benzoyloxyethyl)) | 486.27 |

TABLE 5-continued

| Ex. | T | M/s M+ |
|---|---|---|
| 75 | 4-methylpiperidinium, N-methyl, N-(2-phenoxyethyl) | 458.28 |
| 76 | 4-methylpiperidinium, N-methyl, N-(phenacyl) | 456.24 |
| 77 | 4-methylpiperidinium, N-methyl, N-(hept-2-ynyl) | 446.29 |
| 78 | 4-methylpiperidinium, N-methyl, N-(but-3-enyl) | 392.23 |
| 79 | 4-ethylpiperidinium, N-methyl, N-(3-phenoxypropyl) | 486.33 |
| 80 | 4-ethylpiperidinium, N-methyl, N-(2-phenoxyethyl) | 472.30 |
| 81 | 4-ethylpiperidinium, N-methyl, N-(3-(4-fluorophenoxy)propyl) | 504.32 |
| 82 | 4-ethylpiperidinium, N-methyl, N-(2-benzyloxyethyl) | 486.31 |
| 83 | 4-ethylpiperidinium, N-methyl, N-cinnamyl | 468.30 |
| 84 | 4-ethylpiperidinium, N-methyl, N-(2-phenylethyl) | 456.30 |
| 85 | 4-ethylpiperidinium, N-methyl, N-(3-phenylpropyl) | 470.32 |
| 86 | 4-ethylpiperidinium, N-methyl, N-propargyl | 390.22 |

TABLE 5-continued

| Ex. | T | M/s M+ |
|---|---|---|
| 87 | 4-ethylpiperidinium, N-methyl, N-(hept-2-ynyl) | 460.31 |
| 88 | 4-ethylpiperidinium, N-methyl, N-(2-acetoxyethyl) | 438.29 |
| 89 | 4-ethylpiperidinium, N-methyl, N-(2-benzoyloxyethyl) | 500.30 |
| 90 | 4-ethylpiperidinium, N-methyl, N-(but-3-enyl) | 406.26 |
| 91 | 4-ethylpiperidinium, N-methyl, N-(2-methoxyethyl) | 410.25 |
| 92 | 4-ethylpiperidinium, N-methyl, N-(2-ethoxyethyl) | 424.27 |
| 93 | 4-ethylpiperidinium, N-methyl, N-(2-(2-methoxyethoxy)ethyl) | 454.28 |
| 94 | cis-4-methylpiperidinium, N-methyl, N-(3-phenylpropyl) | 456.07 |
| 95 | cis-4-methylpiperidinium, N-methyl, N-(2-phenoxyethyl) | 458.95 |
| 96a | trans-3-methylpiperidinium, N-methyl, N-(3-phenylpropyl) | 456.1 |
| 96b | trans-3-methylpiperidinium, N-methyl, N-(3-phenylpropyl) | 456.2 |
| 97a | trans-3-methylpiperidinium, N-methyl, N-(2-phenoxyethyl) | 458.11 |

| Ex. | T | M/s M+ |
|---|---|---|
| 97b | [structure: piperidinium with H, CH3, methyl substituent, N+ linked via ethyl-O-phenyl] | 458.15 |

Preparation of Intermediate Compounds

Abbreviations used are as follows: DCM is dichloromethane, DMF is dimethylformamide, and DMSO is dimethylsulphoxide and THF is tetrahydrofuran.

Hydroxy-diphenyl-acetic-acid-1-methyl-piperidin-4-yl-ester

This compound is prepared using the method described in United States patent specification U.S. Pat. No. 3,252,981.

Hydroxy-diphenyl-acetic acid 1-methyl-piperidin-4-ylmethyl ester (1-Methyl-piperidin-4-yl)-methanol (2.58 g, 20 mmol) and hydroxy-diphenyl-acetic acid methyl ester (9.69 g, 40 mmol) are suspended in toluene (65 ml). Molecular sieve 4A (1 g) is added and the mixture is stirred at room temperature for 10 minutes. Sodium (0.08 g) is added and the reaction mixture stirred at 80° C. for 3 hours. Additional sodium (0.1 g) is then added and heating maintained at 80° C. for 18 hours. The reaction mixture is cooled to room temperature, solid filtered off, and washed with ethylacetate. The filtrate is washed once with saturated aqueous NaHCO$_3$ solution (50 ml) and twice with aqueous HCl 1M (25 ml each). The combined acidic aqueous layers are basified with saturated aqueous NaHCO$_3$ solution and solid NaHCO$_3$, the resulting precipitate is removed by filtration, drying under vacuum gives the title product as a white solid (M+H)$^+$:340.09.

Hydroxy-di-thiophen-2-yl-acetic acid 1-methyl-piperidin-4-yl ester a) Oxo-thiophen-2-yl-acetyl chloride To a solution of oxo-thiophen-2-yl-acetic acid (8 g, 51.2 mmol), suspended in DCM (80 ml) and cooled to 5° C., is added oxalylchloride (5.3 ml, 61.5 mmol), followed by DMF (0.1 ml). Stirring is continued for 1 hour at 5° C. and 18 hours at room temperature. The reaction mixture is evaporated to dryness, toluene is then added and the mixture is evaporated once more to give the title compound as a dark oil.

b) Oxo-thiophen-2-yl-acetic acid 1-methyl-piperidin-4-yl ester

To a solution of oxo-thiophen-2-yl-acetyl chloride (29 mmol) at 0 to 5° C. in chloroform (60 ml) is added a solution of 1-methyl-piperidine-4-ol (5.87 g, 29 mmol) in chloroform (60 ml), dropwise with stirring. The resulting mixture is stirred for 2 hours at room temperature. Washing with 10% potassium carbonate solution, water (×2), drying over magnesium sulphate, filtration and evaporation gives the title compound.

c) Hydroxy-di-thiophen-2-yl-acetic acid 1-methyl-piperidin-4-yl ester

A solution of 2-bromothiophene (3.2 ml, 33 mmol) in THF (30 ml) is added dropwise to a mixture of magnesium (0.8 g, 33 mmol) and a single crystal of iodine in THF (30 ml). After addition of just under one half of the 2-bromothiophene the addition is suspended until reaction has initiated (judged by an exotherm). The addition is then completed maintaining the reaction temperature to below 40° C. After the addition is completed the reaction mixture is heated to 70° C. for 1 hour. This mixture is then cooled and added to a solution of oxo-thiophen-2-yl-acetic acid 1-methyl-piperidin-4-yl ester (6.48 g, 25.6 mmol) in THF (80 ml). After the addition is completed the reaction mixture is stirred at room temperature for 1 hour and then heated to reflux for 2 hours. After cooling to room temperature saturated aqueous ammonium chloride solution (100 ml) is added. The solution is extracted with diethylether dried over magnesium sulphate, filtered and concentrated. Purification by flash silica column chromatography gives the title product.

Hydroxy-di-thiophen-2-yl-acetic acid 1-methyl-piperidin-4-ylmethyl ester a) Oxo-thiophen-2-yl-acetyl chloride To a solution of oxo-thiophen-2-yl-acetic acid (8 g, 51.2 mmol), suspended in DCM (80 ml) and cooled to 5° C., is added oxalylchloride (5.3 ml, 61.5 mmol), followed by DMF (0.1 ml). Stirring is continued for 1 hour at 5° C. and 18 hours at room temperature. The reaction mixture is evaporated to dryness, toluene is then added and the mixture evaporated once more to give the title compound as a dark oil.

b) Oxo-thiophen-2-yl-acetic acid 1-methyl-piperidin-4-ylmethyl ester

To a solution of oxo-thiophen-2-yl-acetyl chloride (31.5 mmol) at 0 to 5° C. in chloroform (60 ml) is added a solution of (1-Methyl-piperidin-4-yl)-methanol (4.07 g, 31.5 mmol) in chloroform (60 ml), dropwise maintaining the temperature below 5° C. The resulting mixture is stirred for 2 hours at room temperature. Washing with 10% potassium carbonate solution, water and then drying over magnesium sulphate, filtration and evaporation gives the title compound.

c) Hydroxy-di-thiophen-2-yl-acetic acid 1-methyl-piperidin-4-ylmethyl ester

A solution of 2-bromothiophene (2.15 ml, 22.2 mmol) in THF (15 ml) is added dropwise to a mixture of magnesium (0.54 g, 22.2 mmol) and a single crystal of iodine in THF (15 ml). After addition of just under one half of the 2-bromothiophene the addition is suspended until reaction has initiated (judged by an exotherm). The addition is then completed maintaining the reaction temperature to below 40° C. After the addition is completed the reaction mixture is heated to reflux for 20 minutes. This mixture is then cooled and added to a solution of oxo-thiophen-2-yl-acetic acid 1-methyl-piperidin-4-ylmethyl ester (4.6 g, 17.2 mmol) in THF (40 ml). After the addition is completed the reaction mixture is stirred at room temperature for 1 hour and then heated to reflux for 2.5 hours. After cooling to room temperature saturated aqueous ammonium chloride solution (100 ml) is added together with diethylether. The solution is extracted with diethylether dried over magnesium sulphate, filtered and concentrated. Purification by flash silica column chromatography gives the title product.

Hydroxy-diphenyl-acetic acid
(R)-1-methyl-piperidin-3-yl ester a) (R)-3-Hydroxypiperidine-1-carboxylic acid tert-butyl ester (R)-3-Hydroxypiperidine hydrochloride (6.574 g, 0.048 mol) is dissolved under stirring in aqueous 2M sodium hydroxide solution (65 ml) and cooled to 0° C. A solution of di-tert-butyl dicarbonate (11.44 g, 0.525 mol) in 1,4-dioxane (65 ml) is added dropwise and the reaction mixture is stirred at room temperature for 90 minutes. The reaction mixture is extracted with chloroform (3×150 ml) and the combined organic layers are washed once with water and once with brine, dried over magnesium sulphate, filtered off and evaporated to dryness to give the title compound.

b) (R)-1-Methyl-piperidine-3-ol (R)-3-Hydroxypiperidine-1-carboxylic acid tert-butyl ester (10 g, 0.05 mol) is dissolved in dry THF (50 ml) and cooled to 0° C. under an inert atmosphere. Lithium aluminium hydride, 1M solution in THF, (80 ml, 0.08 mol) is canulated to this solution at 0 to 5° C. After the addition the reaction mixture is warmed to room temperature and stirred over night. The reaction mixture is cooled in an ice bath and Rochelle's salt (5 g) is added and the reaction left stirring for 30 minutes. Afterwards water (10 ml) is added dropwise and the solvent evaporated. The residue is taken up in chloroform (70 ml) and isopropanol (30 ml) and stirred for 1 hour. The solid is filtered off and extracted again. The organic extracts are combined and evaporated to yield the title compound as a pale oil.

c) Hydroxy-diphenyl-acetic acid
(R)-1-methyl-piperidin-3-yl ester

To a mixture of (R)-1-methyl-piperidine-3-ol (4.61 g, 0.040 mol) and hydroxy-diphenyl-acetic acid methyl ester (9.63 g, 0.040 mol) in cyclohexane (50 ml) is added preactivated 4A molecular sieves and the mixture heated to 50° C. Sodium metal (50 mg) is then added and the resulting mixture heated to reflux. After 1 hour further sodium (50 mg) is added and reflux maintained for 5 hours. Concentration, re-dissolution in chloroform and washing with water followed by brine, drying over magnesium sulphate, filtration and evaporation gives a crude product. Purification by vacuum flash silica chromatography (gradient elution: DCM to DCM:methanol 20:1) gives, after evaporation, the title product as a foam.

Hydroxy-di-thiophen-2-yl-acetic acid (R)-1-methyl-piperidin-3-yl ester a) Oxo-thiophen-2-yl-acetyl chloride To a solution of oxo-thiophen-2-yl-acetic acid (8 g, 51.2 mmol), suspended in DCM (80 ml) and cooled to 5° C., is added oxalylchloride (5.3 ml, 61.5 mmol), followed by DMF (0.1 ml). Stirring is continued for 1 hour at 5° C. and 18 hours at room temperature. The reaction mixture is evaporated to dryness, toluene is then added and the mixture evaporated once more to give the title compound as a dark oil.

b) Oxo-thiophen-2-yl-acetic acid (R)-1-methyl-piperidin-3-yl ester

To a solution of oxo-thiophen-2-yl-acetyl chloride (8.9 g, 51.2 mmol) at 5° C. in DCM (50 ml) is added a solution of (R)-1-Methyl-piperidine-3-ol (5.87 g, 51 mmol) in DCM (50 ml), dropwise with stirring over 20 minutes. The resulting mixture is stirred for 18 hours at room temperature. Washing with 1 Molar sodium bicarbonate solution, drying over magnesium sulphate, filtration and evaporation then gives the title compound as a dark oil.

c) Hydroxy-di-thiophen-2-yl-acetic acid (R)-1-methyl-piperidin-3-yl ester

A solution of 2-bromothiophene (0.092 ml, 0.94 mmol) in THF (2 ml) is added to magnesium (0.576 g, 23.7 mmol) followed by a single crystal of iodine. Additional 2-bromothiophene (2.2 ml, 22.8 mmol) in THF (48 ml) is then added dropwise whilst maintaining a gentle reflux. After the addition is completed the reaction mixture is heated to reflux for 1 hour. This mixture is then added to a solution of oxo-thiophen-2-yl-acetic acid (R)-1-methyl-piperidin-3-yl ester (6 g, 23.7 mmol) in THF dropwise with stirring. After the addition is completed the reaction mixture is heated to reflux for 2 hours. After cooling to room temperature saturated aqueous ammonium chloride solution (100 ml) is added followed by water (100 ml). The resulting solution is extracted with ethylacetate (200 ml) and the resulting organic phase extracted with 1 Molar hydrochloric acid (100 ml). Basification of the aqueous layer with sodium carbonate, extraction with ethylacetate, drying over magnesium sulphate, filtration and concentration gives the title product as a brown oil which crystallises on standing.

Hydroxy-diphenyl-acetic acid
(S)-1-methyl-pyrrolidin-2-ylmethyl ester ((S)-1-Methyl-pyrrolidin-2-yl)-methanol (2.38 ml, 20 mmol) and hydroxy-diphenyl-acetic acid methyl ester (7.27 g, 30 mmol) are suspended in toluene (20 ml). Molecular sieve 4A (3 g) is added and the suspension is heated under stirring to 80° C. Sodium (0.46 g, 20 mmol) is added and the reaction mixture stirred at 80° C. for 3 hours. The reaction mixture is cooled to room temperature, solid filtered off, and washed with toluene. The filtrate is washed once with saturated aqueous NaHCO$_3$ solution (50 ml) and twice with aqueous HCl 1M (30 ml each). The combined acidic aqueous layers are adjusted to pH 8 with saturated aqueous NaHCO$_3$ solution. The emulsion is extracted with ethyl acetate (50 ml). The combined ethyl acetate layers are dried over sodium sulphate, filtered off and evaporated to dryness to give the product as a yellow oil that crystallises on standing. (M+H)$^+$: 326.2

Hydroxy-diphenyl-acetic acid (R)-1-methyl-pyrrolidin-2-yl-methyl ester is prepared analogously.

Hydroxy-di-thiophen-2-yl-acetic acid (S)-1-methyl-pyrrolidin-2-ylmethyl ester

To a mixture of molecular sieve 4A, ((S)-1-Methyl-pyrrolidin-2-yl)-methanol (3.71 g, 31.2 mmol) and Hydroxy-di-thiophen-2-yl-acetic acid methyl ester (3.96 g, 15.6 mmol) in toluene (40 ml) is added sodium (65 mg) and the suspension is heated under stirring to 80° C. for 3.5 hours. Additional sodium (65 mg) is then added and the reaction mixture stirred at 80° C. for 16 hours. The reaction mixture is cooled to room temperature, diluted with diethylether (100 ml) and extracted with HCl 1 M (2×100 ml). The combined acidic aqueous layers are washed with diethylether (50 ml) and basified with sodium hydroxide 4 M whilst cooling in ice. The solution is then extracted with ethylacetate and diethylether. The combined organic layers are dried over magnesium sulphate, filtered and evaporated to dryness to give the title product.

Preparation of Specific Examples

Abbreviations used are as follows: DCM is dichloromethane, DMF is dimethylformamide, and DMSO is dimethylsulphoxide, HPLC is high performance liquid chromatography.

Example 1

Cis and trans-4-(2-Hydroxy-2,2-diphenyl-acetoxy)-1-methyl-1-(2-phenoxy-ethyl)-piperidinium bromide (1a,1b)

Hydroxy-diphenyl-acetic-acid-1-methyl-piperidin-4-yl-ester (0.5 g, 1.5 mmol) and (2-bromo-ethoxy)-benzene (0.37 g, 1.8 mmol) is dissolved in DMF and heated to 40° C. for 24 hours. Additional (2-bromo-ethoxy)-benzene (0.18 g, 0.9 mmol) and 100 mg of potassium carbonate is added and stirring continued at 40° C. for another 24 hours. The temperature is raised to 60° C. and (2-bromo-ethoxy)-benzene (0.1 g, 0.5 mmol) is added and stirring continued at this temperature for 24 hours. A further portion of (2-bromo-ethoxy)-benzene (0.1 g, 0.5 mmol) is added and stirring continued for 16 hours at 60° C. The reaction mixture is filtered and the solvent evaporated. The resulting oil is taken up in acetonitrile and the product crystallised to give a mixture (1a) of cis and trans isomers. The solid is filtered off and recrystallised twice from acetonitrile to yield the trans diastereoisomer (1b) as a white solid.

Example 2

(S)-2-(2-Hydroxy-2,2-diphenyl-acetoxymethyl)-1-methyl-1-oct-2-ynyl-pyrrolidinium trifluoroacetate 200 µl of a 1.1 M solution of 1-bromooct-2-yne in DMSO is added to 200 µl of a 0.368 M solution of hydroxy-diphenyl-acetic acid (S)-1-methyl-pyrrolidin-2-ylmethyl ester in DMSO with a robotic liquid handler in a 96 well plate. The well plate is sealed and placed in an oven at 40° C. for 48 hours. The well plate is cooled to room temperature and the reaction mixture purified by mass directed preparative HPLC eluting with acetonitrile:water:trifluoroacetic acid to yield the title compound as an oil. The product is isolated as a mixture of diastereoisomers varying in stereochemistry at the quaternary nitrogen atom. The counterion present after preparative HPLC is a varying mixture of bromide and trifluoroacetate.

The compounds of Examples 3 to 24 and 49 to 62 are prepared analogously using the appropriate starting compounds.

Example 25

4-(2-Hydroxy-2,2-diphenyl-acetoxymethyl)-1-methyl-1-(2-oxo-2-phenyl-ethyl)-piperidinium trifluoroacetate 200 µl of a 1.1 M solution of 2-Bromo-1-phenyl-ethanone in DMSO is added to 200 µl of a 0.368 M solution of Hydroxy-diphenyl-acetic acid 1-methyl-piperidin-4-ylmethyl ester in DMSO with a robotic liquid handler in a 96 well plate. The well plate is sealed and placed in an oven at 40° C. for 48 hours. The well plate is cooled to room temperature and the reaction mixture purified by mass directed preparative HPLC eluting with acetonitrile:water:trifluoroacetic acid to yield the title compound as an oil. The product is isolated as a mixture of diastereoisomers varying in stereochemistry at the quaternary nitrogen atom. The counterion present after preparative HPLC is a varying mixture of bromide and trifluoroacetate.

The compounds of Examples 26 to 42 and 63 to 93 are prepared analogously using the appropriate starting compounds.

Examples 43 and 44

Cis and trans 4-(2-Hydroxy-2,2-diphenyl-acetoxy)-1-methyl-1-(3-phenoxy-propyl)-piperidinium bromide Hydroxy-diphenyl-acetic-acid-1-methyl-piperidin-yl-ester (2.44 g, 7.52 mmol) and (3-Bromo-propoxy)-benzene (1.78 ml, 11.3 mmol) are dissolved in DMF (16 ml) and stirred at 50° C. for 20 hours. Concentration gives a white solid which is triturated with acetonitrile and dried under vacuum. Recrystallisation from acetonitrile allows the isolation of predominantly one diastereoisomer from the crystals formed. The other diastereoisomer is predominantly precipitated from the filtrate after further concentration. These two solids represent the cis and trans isomers of the title compound.

Example 45

1-[2-(4-Benzyloxycarbonyl-phenyl)-ethyl]-4-(2-hydroxy-2,2-diphenyl-acetoxy)-1-methyl-piperidinium bromide Hydroxy-diphenyl-acetic-acid-1-methyl-piperidin-4-yl-ester (1.56 g, 4.8 mmol) and 4-(2-bromo-ethyl)-benzoic acid benzyl ester (2.3 ml, 7.21 mmol) are dissolved in DMF (5 ml) and stirred at 50° C. for 20 hours, followed by heating at 60° C. for 5 hours. Concentration and purification twice by C-18 reverse phase chromatography (eluant: water/acetonitrile) gives the title compound as a mixture of diastereoisomers.

Example 46

(1S/R,3R)-3-(2-Hydroxy-2,2-diphenyl-acetoxy)-1-methyl-1-(2-phenoxy-ethyl)-piperidinium bromide (46a), (1S,3R)-3-(2-Hydroxy-2,2-diphenyl-acetoxy)-1-methyl-1-(2-phenoxy-ethyl)-piperidinium bromide (46b) and (1R,3R)-3-(2-Hydroxy-2,2-diphenyl-acetoxy)-1-methyl-1-(2-phenoxy-ethyl)-piperidinium bromide (46c)

Hydroxy-diphenyl-acetic acid (R)-1-methyl-piperidin-3-yl ester (2.25 g, 0.00692 mol) and (2-bromo-ethoxy)-benzene (2.08 g, 0.0103 mol) are dissolved in acetonitrile (3 ml) and stirred at 60° C. for 72 hours to give the (1S/R,3R) mixture (46a). The reaction mixture is cooled to room temperature and evaporated to dryness producing a white foam. Trituration is then performed by adding acetone to the foam, which is then sonicated, heated to reflux and left to cool to room temperature. The suspension is filtered off dried and the resulting solid recrystallised twice from acetonitrile containing a small amount of water to give (1S,3R)-diastereoisomer (46b) as a white solid. The mother liquor from the initial acetone trituration is then taken and evaporated down to give a solid. The residue is purified by flash chromatography over C18 silica gel (70 g) using a gradient of water/acetonitrile 100/0 to 0/100 over 40 minutes at 20 ml/min. The product containing fractions are combined and evaporated down to yield predominately the (1R,3R)-diastereoisomer (46c) as a white solid.

Example 47

(1S/R,3R)-3-(2-Hydroxy-2,2-diphenyl-acetoxy)-1-methyl-1-(3-phenyl-propyl)-piperidinium bromide (47a) and (1R,3R)-3-(2-Hydroxy-2,2-diphenyl-acetoxy)-1-methyl-1-(3-phenyl-propyl)-piperidinium bromide (47b)

Hydroxy-diphenyl-acetic acid (R)-1-methyl-piperidin-3-yl ester (3.0 g, 0.00923 mol) and (3-bromo-propyl)-benzene (2.12 ml, 0.0138 mol) are dissolved in acetonitrile (3 ml) and stirred at 60° C. for 24 hours. At this point HPLC/MS shows the formation of the (1S/R, 3R) mixture (47a). Standing at room temperature for 72 hours results in the precipitation of a white solid. Two consecutive recrystallisations from acetonitrile give the (1R,3R)-title compound (47b).

Example 48

(1R/S,3R)-3-(2-Hydroxy-2,2-diphenyl-acetoxy)-1-methyl-1-(2-phenoxy-propyl)-piperidinium bromide Hydroxy-diphenyl-acetic acid (R)-methyl-piperidin-3-yl ester (1.7 g, 0.00523 mol) and (3-bromo-propoxy)-benzene (1.2 ml, 0.00781 mol) are dissolved in acetonitrile (2 ml) and stirred at 60° C. over night. The reaction mixture is cooled to room temperature and evaporated to dryness. The residue is taken up in DCM and extracted with water. The aqueous layer is washed with DCM (3×20 ml) and evaporated to dryness. The residue is purified by flash chromatography over C18 silica gel (70 g) using a gradient of water/acetonitrile 100/0 to 0/100 over 25 minutes at 20 ml/min. The product containing fractions were combined and evaporated to yield 700 mg of the title compound as a white foam.

Example 94

Trans 4-(2-hydroxy-2,2-di-thiophen-2-yl-acetoxy)-1-methyl-1-(3-phenyl-propyl)-piperidinium bromide Hydroxy-di-thiophen-2-yl-acetic acid 1-methyl-piperidin-4-yl ester (1.5 g, 4.44 mmol) and (3-bromo-propyl)-benzene (1.4 ml, 8.88 mmol) are dissolved in DMF (5 ml) and stirred at 50° C. for 16 hours. The resultant solid is separated by filtration washed with DMF (5 ml) and dried under high vacuum giving a 1:1 cis/trans mixture of diastereoisomers (as alternatively isolated in Example 67.) Two further recrystallisations from DMF give the title compound (trans diastereoisomer).

Example 95

Trans-4-(2-Hydroxy-2,2-dithiophen-2-yl-acetoxy)-1-methyl-1-(2-phenoxy-ethyl)-piperidinium bromide Hydroxy-di-thiophen-2-yl-acetic acid 1-methyl-piperidin-4-yl ester (1.5 g, 0.00444 mol) and 2-phenoxy ethylbromide (1.79 g, 0.00888 mol) are dissolved in DMF (5 ml) and stirred at 50° C. for 16 hours. The reaction mixture is evaporated to dryness to give the cis/trans mixture and the residue taken up in acetonitrile (10 ml) and stirred at room temperature for 10 minutes. The suspension is filtered and the solid recrystallised from acetonitrile to give the trans isomer (139) as white solid.

Example 96

(1R,3R)-3-(2-3-Hydroxy-2,2-dithiophen-2-yl-acetoxy)-1-methyl-1-(3-phenyl-propyl)-piperidinium bromide (96a) and (1S,3R)-3-(2-Hydroxy-2,2-dithiophen-2-yl-acetoxy)-1-methyl-1-(3-phenyl-propyl)-piperidinium bromide (96b)

Hydroxy-di-thiophen-2-yl-acetic acid (R)-1-methyl-piperidin-3-yl ester (2.1 g, 0.00623 mol) is dissolved in acetonitrile (5 ml) at 60° C. and 1-bromo-3-phenylpropane (1.43 ml, 0.00934 mol) is added dropwise. After 18 hours stirring at 60° C., the white solid is broken up and stirring continued for another 8 hours at this temperature. The suspension is cooled to room temperature and the solid filtered off. The solid is recrystallised from 3 ml of acetonitrile containing 2 drops of water to yield (1R,3R)-3-(2-Hydroxy-2,2-di-thiophen-2-yl-acetoxy)-1-methyl-1-(3-phenyl-propyl)-piperidinium bromide (96a) as a white solid. The reaction mixture mother liquid is evaporated to dryness and the residue is purified by flash chromatography over C18 silica gel (70 g) using a gradient of water/acetonitrile 10010 to 0/100 over 25 minutes at 20 ml/min. The product containing fractions are combined and evaporated to dryness to yield (1S,3R)-3-(2-hydroxy-2, 2-di-thiophen-2-yl-acetoxy)-1-methyl-1-(3-phenyl-propyl)-piperidinium bromide (96b) as a white amorphous solid.

Example 97

(1R/S,3R)-3-(2-Hydroxy-2,2-dithiophen-2-yl-acetoxy)-1-methyl-1-(2-phenoxy-ethyl)-piperidinium bromide (97a) and (1R,3R)-3-(2-Hydroxy-2,2-dithiophen-2-yl-acetoxy)-1-methyl-1-(2-phenoxy-ethyl)-piperidinium bromide (97b)

Hydroxy-di-thiophen-2-yl-acetic acid (R)-1-methyl-piperidin-3-yl ester (0.57, 0.00169 mol) is dissolved in acetonitrile (3 ml) at 60° C. and 2-phenoxyethyl bromide (0.51 g, 0.00254 mol) in Acetonitrile (1 ml) is added dropwise. The reaction mixture is refluxed for 96 hours, cooled to room temperature and left in the refrigerator. This gives an approximately 1:1 mixture of isomers (1R/S,3R)-3-(2-hydroxy-2,2-dithiophen-2-yl-acetoxy)-1-methyl-1-(2-phenoxy-ethyl)-piperidinium bromide (97a). The suspension is filtered off and washed with cold acetonitrile to yield (1R,3R)-3-(2-hydroxy-2,2-dithiophen-2-yl-acetoxy)-1-methyl-1-(2-phenoxyethyl)-piperidinium bromide (97b) as a white solid.

The invention claimed is:
1. A compound of formula I

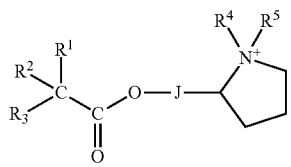

in salt or zwitterionic form wherein
- $R^1$ and $R^3$ are each independently a $C_3$-$C_{15}$-carbocyclic group or a 5- to 12-membered heterocyclic group having at least one ring heteroatom selected from nitrogen, oxygen and sulphur;
- $R^2$ is hydroxy;
- J is $C_1$-$C_2$-alkylene;
- $R^4$ is $C_1$-$C_4$-alkyl;
- $R^5$ is $C_1$-alkyl substituted by —CO—$R^6$, or —CO—NH—$R^6$,
- or $R^5$ is $C_2$-$C_{10}$-alkyl substituted by —O—$R^6$, —O—CO—$R^6$, or —$R^8$,
- or $R^5$ is $C_2$-$C_{10}$-alkenyl or $C_2$-$C_{10}$-alkynyl optionally substituted by —$R^8$;
- $R^6$ is a $C_3$-$C_{15}$-carbocyclic group,
- or $R^6$ is $C_1$-$C_{10}$-alkyl optionally substituted by $C_1$-$C_{10}$-alkoxy, —O—$R^8$ or a $C_3$-$C_{15}$-carbocyclic group; and
- $R^8$ is a $C_3$-$C_{15}$-carbocyclic group.

2. A compound according to claim 1, wherein
- $R^1$ and $R^3$ are each independently a $C_3$-$C_{10}$-carbocyclic group, preferably phenyl, or a 5- to 9-membered heterocyclic group having at least one ring heteroatom selected from nitrogen, oxygen and sulphur, preferably thienyl;
- $R^2$ is hydroxy;
- J is $C_1$-$C_2$-alkylene;
- $R^4$ is $C_1$-$C_4$-alkyl;
- $R^5$ is $C_1$-alkyl substituted by —CO—$R^6$ or —CO—NH—$R^6$,
- or $R^5$ is $C_2$-$C_4$-alkyl substituted by —O—$R^6$, —O—CO—$R^6$ or —$R^8$,
- or $R^5$ is $C_2$-$C_4$-alkenyl or $C_2$-$C_8$-alkynyl optionally substituted by —$R^8$;
- $R^6$ is a $C_3$-$C_{10}$-carbocyclic group, preferably phenyl,
- or $R^6$ is $C_1$-$C_{15}$-alkyl optionally substituted by $C_1$-$C_4$-alkoxy, O—$R^8$ or a $C_3$-$C_{10}$-carbocyclic group; and
- $R^8$ is a $C_3$-$C_{10}$-carbocyclic group, preferably phenyl.

3. A compound according to claim 1, which is also a compound of formula XVI

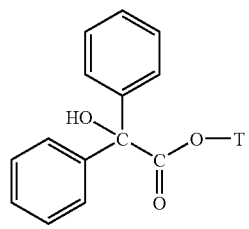

XVI where T is as shown in the following table:

| T |
|---|
| 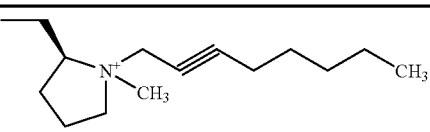 |

-continued

| T |
|---|
| 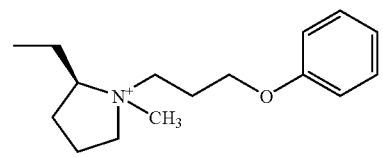 |
| 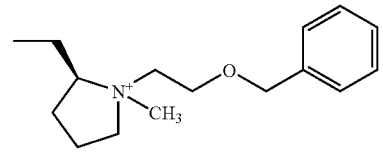 |
| 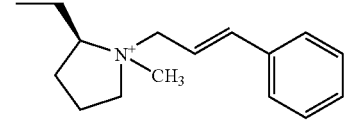 |
| 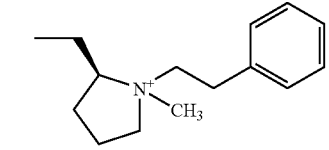 |
| 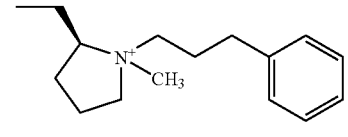 |
| 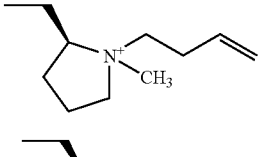 |
| 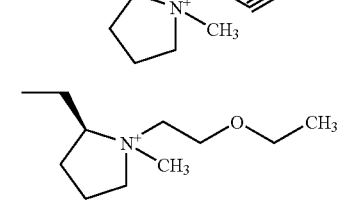 |
| 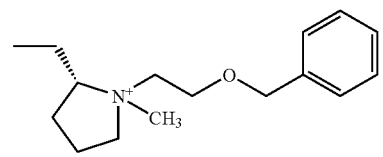 |
| 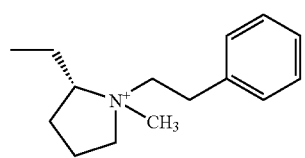 |

-continued
| T |
|---|
| 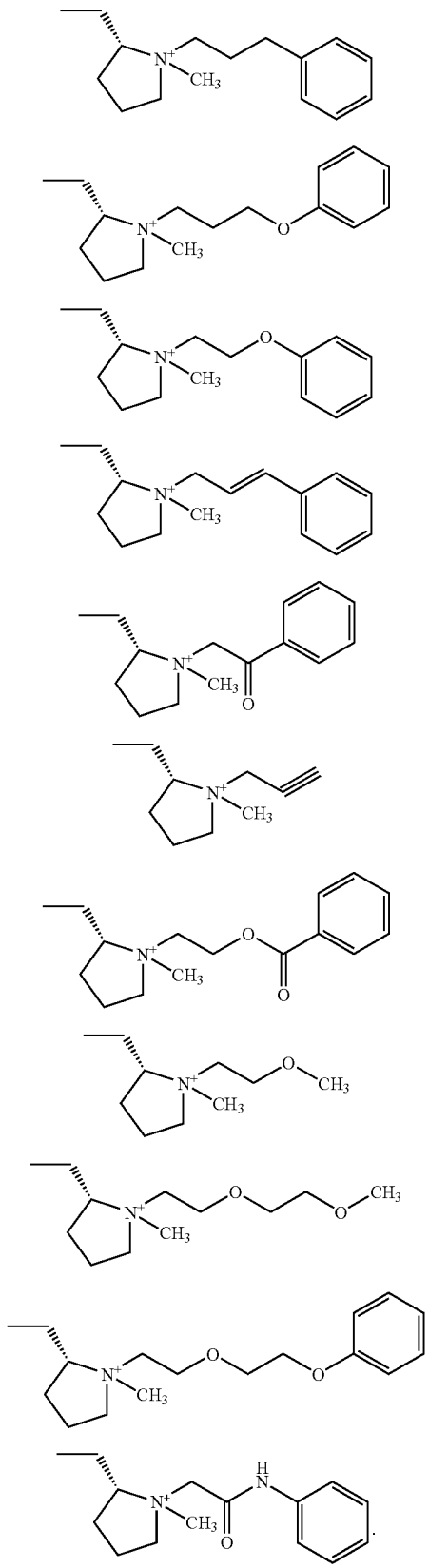 |
4. A compound according to claim 1, which is also a compound of formula XVII
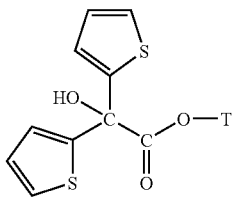
where T is as shown in the following table:
| T |
|---|
| 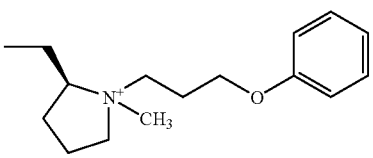 |

-continued

T

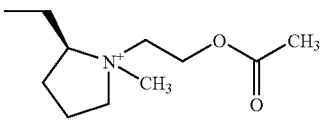

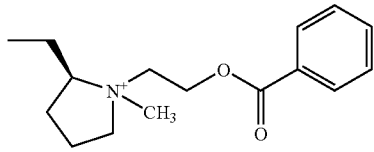

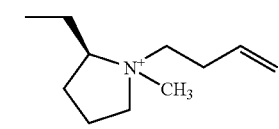

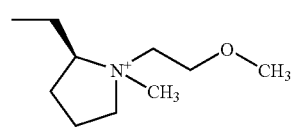

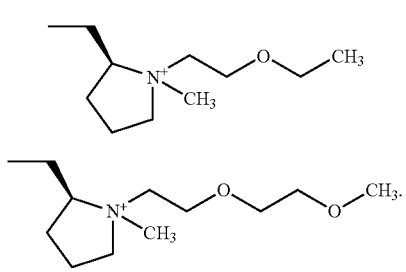

5. A pharmaceutical composition comprising as active ingredient a compound according to claim 1.

6. A process for the preparation of a compound of formula I as claimed in claim 1 which comprises:

(i) (A) reacting a compound of formula II

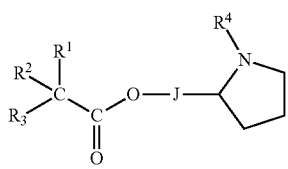

or a protected form thereof where $R^1$, $R^2$, $R^3$, $R^4$, and J, are as defined in claim 1, with a compound of formula III $$X—R^5 \quad \text{III}$$

where $R^5$ is as defined in claim 1 and X is chloro, bromo or iodo;

(B) reacting a compound of formula IV

IV or a protected form thereof where $R^1$, $R^2$, $R^3$, $R^5$ and J are as defined in claim 1, with a compound of formula V $$X—R^4 \quad \text{V}$$

where $R^4$ is as defined in claim 1 and X is chloro, bromo or iodo; and (ii) recovering the product in salt or zwitterionic form.

7. A method of treating an inflammatory or obstructive airways disease in a subject in need of such treatment, which comprises administering to said subject an effective amount of a compound of formula I as defined in claim 1 in free form or in the form of a pharmaceutically acceptable salt.

8. A compound of formula VI in salt or zwitterionic form wherein
$R^1$ and $R^3$ are each independently a $C_3$-$C_{15}$-carbocyclic group or a 5- to 12-membered heterocyclic group having at least one ring heteroatom selected from nitrogen, oxygen and sulphur;
$R^2$ is hydroxy;
J is $C_1$-$C_2$-alkylene;
$R^4$ is $C_1$-$C_4$-alkyl; and
Q is $C_1$-$C_{10}$-alkylene.

9. A pharmaceutical composition according to claim 5 wherein the compound is a single enantiomer.

* * * * *